US007371526B2

(12) United States Patent
Zon et al.

(10) Patent No.: US 7,371,526 B2
(45) Date of Patent: May 13, 2008

(54) METHOD AND MATERIALS FOR BISULFITE CONVERSION OF CYTOSINE TO URACIL

(75) Inventors: Gerald Zon, San Carlos, CA (US); Victoria L. Boyd, San Carlos, CA (US)

(73) Assignee: Applera Corporation, Foster City, CA (US)

( * ) Notice: Subject to any disclaimer, the term of this patent is extended or adjusted under 35 U.S.C. 154(b) by 442 days.

(21) Appl. No.: 10/926,531

(22) Filed: Aug. 26, 2004

(65) Prior Publication Data

US 2005/0095623 A1 May 5, 2005

Related U.S. Application Data

(60) Provisional application No. 60/499,082, filed on Aug. 29, 2003, provisional application No. 60/523,056, filed on Nov. 17, 2003.

(51) Int. Cl.
*C12Q 1/68* (2006.01)
*G01N 33/53* (2006.01)
*C07H 21/00* (2006.01)

(52) U.S. Cl. .................. 435/6; 536/23.1; 436/808; 435/810

(58) Field of Classification Search ............... 435/6, 435/810; 536/23.1; 436/808
See application file for complete search history.

(56) References Cited

U.S. PATENT DOCUMENTS

| | | | |
|---|---|---|---|
| 6,214,556 | B1 | 4/2001 | Olek et al. |
| 6,251,594 | B1 | 6/2001 | Gonzalgo et al. |
| 6,331,393 | B1 | 12/2001 | Laird et al. |
| 6,511,810 | B2 | 1/2003 | Bi et al. |
| 7,262,013 | B2 | 8/2007 | Boyd et al. |
| 2004/0121359 | A1 | 6/2004 | Berlin |
| 2004/0152080 | A1 | 8/2004 | Berlin et al. |
| 2004/0241704 | A1 | 12/2004 | Markert-Hahn et al. |
| 2005/0089898 | A1 | 4/2005 | Zon et al. |
| 2005/0095623 | A1 | 5/2005 | Zon et al. |
| 2005/0153308 | A1 | 7/2005 | Zon et al. |
| 2006/0063189 | A1 | 3/2006 | Zon |

FOREIGN PATENT DOCUMENTS

| | | |
|---|---|---|
| EP | 1394173 A1 | 3/2004 |
| JP | 1995/265082 A | 10/1995 |
| WO | WO02/30944 | 4/2002 |
| WO | WO 02/31186 A | 4/2002 |
| WO | WO03/031649 A2 | 4/2003 |
| WO | WO 2004/067545 A | 8/2004 |
| WO | WO 2005/021563 A | 3/2005 |

OTHER PUBLICATIONS

U.S. Appl. No. 60/499,113, filed Aug. 29, 2003, Zon.
U.S. Appl. No. 60/520,942, filed Nov. 17, 2003, Zon.
U.S. Appl. No. 60/499,106, filed Aug. 29, 2003, Zon.
U.S. Appl. No. 60/523,054, filed Nov. 17, 2003, Zon.
U.S. Appl. No. 60/499,082, filed Aug. 29, 2003, Zon.
U.S. Appl. No. 60/523,056, filed Nov. 17, 2003, Zon.
U.S. Appl. No. 60/498,996, filed Aug. 29, 2003, Zon.
U.S. Appl. No. 60/520,941, filed Nov. 17, 2003, Zon.
Shapiro and Klein, "Reactions of Cytosine Derivatives With Acidic Buffer Solutions", Biochemistry, vol. 6, No. 11, Nov. 1967, pp. 3576-3582.
Shapiro et al., "Reactions of Uracil and Cytosine Derivatives With Sodium Bisulfite. A Specific Deamination Method", Journal of the American Chemical Society/92:2/Jan. 28, 1970.
Hayatsu et al., "Reaction of Sodium Bisulfite With Uracil, Cytosine, and Their Derivatives", Biochemistry, vol. 9, No. 14, 1970, pp. 2858-2865.
Shapiro and Weisgras, "Bisulfite-Catalyzed Transamination of Cytosine and Cytidine", Biochemical and Biophysical Research Communications, vol. 40, No. 4, 1970, pp. 839-843.
Shapiro et al., "Nucleic Acid Reactivity and Conformation", The Journal of Biological Chemistry, vol. 248, No. 11, Issue of Jun. 10, pp. 4060-4064, 1973.
Shapiro et al., "Deamination of Cytosine Derivatives by Bisulfite. Mechanism of the Reaction", Journal of the American Chemical Society/96:3/Feb. 6, 1974.
Hikoya Hayatsu, "Bisulfite Modification of Nucleic Acids and Their Constituents", Prog Nucleic Acid Res Mol Biol, 1976, 16 75-124.
Wang et al., "Comparison of Bisulfite Modification of 5-Methyldeoxycytidine and Deoxycytidine Residues" Nucleic Acids Research, vol. 8, No. 20, 1989, pp. 4776-4790.
Miller and Cushman, "Selective Modification of Cytosines in Oligodeoxyribonucleotides", Bioconjugate Chem 1992, 3, 74-79.
Frommer et al., "A Genomic Sequencing Protocol That Yields a Positive Display of 5-Methylcytosine Residues in Individual DNA Strands", Proc. Natl. Acad. Sci. USA, vol. 89, pp. 1827-1831, Mar. 1992, Genetics.
Kumar et al., "Immunoaffinity Chromatography to Isolate Methylated DNA Using Immobilized Anti-5 Methyl Cytosine Antibody", Biotechnology Techniques, vol. 5, No. 6, 469-470 (1991).

(Continued)

*Primary Examiner*—Jezia Riley
(74) *Attorney, Agent, or Firm*—Michael A. Patane; Shirley A. Recipon

(57) ABSTRACT

The invention provides methods and materials for conversion of cytosine to uracil. In some embodiments, a nucleic acid, such as gDNA, is reacted with at least one bisulfite salt having the formula $X^+HSO_3^-$ or $Y^{+2}(HSO_3^{31})_2$; wherein $X^+$ is ammonium ion, a tetraalkyl ammonium ion, or a group 1A ion other than sodium; and $Y^{+2}$ is a group 2A ion or a group 7B ion; under conditions effective to convert at least one cytosine nucleobase to a uracil nucleobase. In some embodiments, $X^+$ comprises at least one of lithium ion, potassium ion, ammonium ion, tetraalkylammonium ion, magnesium ion, manganese ion and calcium ion. In some embodiments, the reacting is performed optionally in the presence of a polyamine catalyst and/or a quaternary amine catalyst. Also provided are kits that can be used to carry out methods of the invention.

19 Claims, No Drawings

OTHER PUBLICATIONS

Molander et al., "Bisulfite Ion-Catalyzed Transamination of Cytosine Residues With α, w-Alkanediamines: The Effect of Chain Length on the Reaction Kinetics", Bioconjugate Chem. 1993, 4, 362-365.

Clark et al., "High Sensitivity Mapping of methylated Cytosines", 2990-2997, Nucleic Acids Research, 1994, vol. 22, No. 15.

Paul and Clark, "Cytosine Methylation: Quantitation by Automated Genomic Sequencing and Genescan™ Analysis", BioTechniques 21:126-133 (Jul. 1996).

Olek et al., "A Modified and Improved Method for Bisulphite Based Cytosine Methylation Analysis", 5064-5066, Nucleic Acids Research, 1996, vol. 24, No. 24.

Herman et al., "Methylation-specific PCR: A Novel PCR Assay for Methylation Status of CpG Islands", Proc. Natl. Acad. Sci, USA, vol. 93, pp. 9821-9826, Sep. 1996, Medical Sciences.

Rein et al., "Active Mammalian Replication Origins Are Associated With a High-Density Cluster of $^m$CpG Dinulceotides", Molecular and Cellular Biology, Jan. 1997, vol. 17, No. 1, p. 416-426.

Paulin et al., "Urea Improves Efficiency of Bisulphite-Mediated Sequencing of 5'-Methylcytosine in Genomic DNA", Nucleic Acids Research, 1998, vol. 26, No. 21, 5009-5010.

Warnecke et al., "Bisulfite Sequencing in Preimplantation Embryos: DNA Methylation Profile of the Upstream Region of the Mouse Imprinted H19 Gene", Genomics 51, 182-190 (1990), Article No. GE985371.

Oakeley, E., et al., "Quantification of 5-Methylcytosine in DNA by the Chloroacetaldehyde Reaction", BioTechniques 27:744-752 (Oct. 1999).

Oakeley, "DNA Methylation Analysis: A Review of Current Methodologies", Pharmacology & Therapeutics 84 (1999) 389-400.

Thomassin et al., "Identification of 5-Methylcytosine in Complex Genomes", Methods, 19, 465-475 (1999).

Grunau et al., "Bisulfite Genomic Sequencing: Systematic Investigation of Critical Experimental Parameters", Nucleic Acids Research, 2001, vol. 29, No. 13, e65.

Kerjean et al., "Bisulfite Genomic Sequencing of Microdissected Cells", Nucleic Acids Research, 2001, vol. 29, No. 21 e106.

Trinh et al., "DNA Methylation Analysis by MethyLight Technology", Methods 25, 456-462 (2001).

Balog et al., "Parallel Assessment of CpG Methylation by Two-Color Hybridization With Oligonucleotide Arrays", Analytical Biochemistry, 309 (2002) 301-310.

Rand et al., "Conversion-Specific Detection of DNA Methylation using Real-Time Polymerase Chain Reaction (ConLight-MSP) to Avoid False Positives", Methods, 27 (2002), 114-120.

Frigola et al., "Methylome Profiling of Cancer Cells by Amplification of Inter-Methylated Sites (AIMS)", Nucleic Acids Research, 2002, vol. 30, No. 7 e28.

Fraga and Esteller, "DNA Methylation: A Profile of Methods and Applications", BioTechniques 33:632-649 (Sep. 2002).

El-Maarri et al., "A Rapid, Quantitative, Non-Radioactive Bisulfite-SNuPE-IP RP HPLC Assay for Methylation Analysis at Specific CpG Sites", Nucleic Acids Research. 2002, vol. 30, No. 6, e25.

Li and Dahiya, "MethPrimer: Designing Primers for Methylation PCRs", Bioinformatics, vol. 18, No. 11, 2002, pp. 1427-1431.

Okamoto et al., "Site-Specific Discrimination of Cytosine and 5-Methylcytosine in Duplex DNA by Peptide Nucleic Acids", JACS Communications (Apr. 10, 2002).

Friso et al., "A Method to Assess Genomic DNA Methylation Using High-Performance Liquid Chromatography/Electrospray Ionization Mass Spectrometry", Anal. Chem. 2002, 74, 4526-4531.

Mills and Ramsahoye, "DNA Methylation Protocols", Methods in Molecular Biology, vol. 200, (2002).

Ushijima et al., "Fidelity of the Methylation Pattern and Its Variation in the Genome", Genome Research, (2003), pp. 868-874.

Humeny, A.., et al., Detection and analysis of enzymatic DNA methylation of oligonucleotide substrates by matrix-assisted laser desorption ionization time-of-flight mass spectrometry, Anal. Biochem. 313 (2003) 160-166.

Kinoshita, H., et al., Screening hypermethylated regions by methylation-sensitive single-strand conformational polymorphism, Anal. Biochem. 278 (2000) 165-169.

Kubareva et al., "Determination of Methylation Site of DNA-Methyl-Transferase Nylax by a Hybrid Method," Biotechniques, Eaton Publishing, Natick, U.S., vol. 33, No. 3, Sep. 2002, pp. 526-531.

Boyd, et al., Bisulfite conversation of genomic DNA for methylation analysis: protocol simplification with higher recovery applicable to limited samples and increased throughput, Analytical Biochemistry, Academic Press, San Diego, CA, U.S., vol. 326, No. 2, Mar. 15, 2004, pp. 278-280.

Komiyama, et al., "Catalysis of diethylenetriamine for bisulfite-induced deamination of cytosine in oligodeoxyribonucleotides," *Tetrahedron Letters* (1994) 35(44): 8185-8188.

International Search Report mailed Jan. 31, 2005 from International Application No. PCT/US2004/028089, published as WO/2005/021803.

International Search Report mailed May 18, 2005 from International Application No. PCT/US04/28070, published as WO/2005/021778.

International Search Report mailed Apr. 15, 2005 from International Application No. PCT/US04/27992, published as WO/2005/021563.

International Search Report mailed Jun. 27, 2005 from International Application No. PCT/US2004/028032, published as WO/2005/021802.

EZ DNA Methylation Kit™, Instructions, Zymo Research, Mar. 11, 2003.

METHOD AND MATERIALS FOR BISULFITE CONVERSION OF CYTOSINE TO URACIL

This application claims benefit of priority to US Provisional Application Ser. Nos. 60/499,082, filed Aug. 29, 2003 and 60/523,056 filed Nov. 17, 2003, each of which is hereby incorporated by reference.

FIELD

The invention relates generally to methods and materials for the specific conversion of cytosine to uracil.

BACKGROUND

Assessment of methylation of DNA is useful in many research, diagnostic, medical, forensic, and industrial fields. Particularly, methylation of cytosine in genomic DNA has been correlated with lack of gene expression, and in some instances can be indicative of early and frequent alterations found in some cancers. Thus, the ability to assess the methylation status of DNA is significant.

Key to this assessment is converting cytosine to uracil. One basic method for such conversion, employing sodium bisulfite, is well known. Over the years, the method has been improved in attempts to overcome disadvantages that include tedious procedures, lengthy reaction times, and DNA degradation. The most commonly used protocol is taught by J. Herman, *Proc. Natl. Acad. Sci.* 93, 9821-26 (1996), incorporated herein by reference in its entirety. This method involves denaturation, reaction with sodium bisulfite in the presence of hydroquinone, and subsequent completion of the modification by treatment with NaOH. Despite the attempts to improve the protocol, current procedures require pre-denaturation of the genomic DNA (gDNA) to single stranded DNA (ssDNA), preparation of fresh solutions of sodium bisulfite (NaHSO$_3$), typically about 3M, and inclusion of an antioxidant (e.g., hydroquinone). The protocol also involves long reaction times and tedious clean-up procedures.

In addition, the currently employed sodium bisulfite protocols are plagued by reports of incomplete conversion, irreproducible results, and other problems. In some cases, the reaction can result in significant DNA degradation (reportedly as high as 96%), making it difficult to obtain enough sample for further analysis. See. S. J. Clark et al. *Nucleic Acid Research* 2001, 29 no. 13, e65. Given the importance of assessment of DNA methylation, it can be seen that there is a need for improved methodologies for conversion of cytosine to uracil.

It has been discovered that bisulfite methods that employ magnesium bisulfite, polyamine compounds, and/or quaternary amine compounds provide useful alternatives to sodium bisulfite conversion reactions. These discoveries are the subjects of co-owned applications entitled "Method And Materials For Polyamine Catalyzed Bisulfite Conversion Of Cytosine To Uracil" (U.S. application Ser. No. 60/499,113 filed Aug. 29, 2003, and also application Ser. No. 60/520,942 having the same title and filed Nov. 17, 2003), "Method And Materials For Quaternary Amine Catalyzed Bisulfite Conversion Of Cytosine To Uracil" (U.S. application Ser. No. 60/499,106 filed Aug. 29, 2003, and also application Ser. No. 60/523,054 having the same title and filed Nov. 17, 2003), and "Method and Materials for Bisulfite Conversion of Cytosine to Uracil" (U.S. application Ser. No. 60/499,082 filed Aug. 29, 2003, all of which are hereby incorporated by reference in their entirety. Improvements in clean-up procedures associated with conversion of cytosine to uracil are also the subject of co-owned applications entitled "Improved Bisulfite Method" (U.S. application Ser. No. 60/498,996 filed Aug. 29, 2003 and also application Ser. No. 60/520,941 having the same title and filed Nov. 17, 2003) all of which are hereby incorporated by reference in their entirety.

SUMMARY

In certain embodiments, methods are provided for converting cytosine nucleobases to uracil nucleobases by using a catalyzed bisulfite reaction. In some embodiments, the present invention provides methods for the conversion of cytosine to uracil in a nucleic acid comprising the steps of reacting a nucleic acid comprising at least one cytosine nucleobase with at least one bisulfite salt having the formula X$^+$HSO3$^-$ or Y$^{+2}$(HSO3$^-$)$_2$; wherein X$^+$ is ammonium ion, a tetraalkyl ammonium ion, or a group 1A ion other than sodium; and Y$^{+2}$ is a group 2A ion or a group 7B ion; under conditions effective to convert at least one cytosine nucleobase to a uracil nucleobase.

In some embodiments, X$^+$ comprises at least one of lithium ion, potassium ion, ammoninium ion, tetraalkylammonium ion, magnesium ion, manganese ion and calcium ion. In some embodiments, the reacting is performed in the presence of a polyamine catalyst. In some such embodiments, the polyamine catalyst has the Formula I or II:

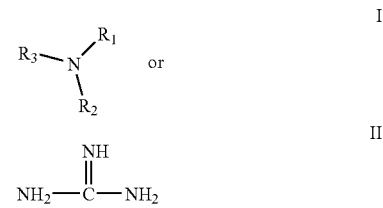

or a salt or derivative thereof, wherein R$_1$, R$_2$ and R$_3$ re each independently
—[—(CH$_2$)$_n$—NH—]$_q$—X; n is 1 to 4; q is 0-3; and X is H or C$_{1-4}$ alkyl; provided that at least one q is not 0.

In some embodiments, the polyamine catalyst comprises at least one of triamines and tetraamines. In further embodiments, the catalyst comprises at least one of diethylene triamine, guanidine and their salts and derivatives. In further embodiments, R$_1$ and R$_2$ are each —(CH$_2$)$_2$—NH$_2$; and R$_3$ is H. In some embodiments, the catalyst is guanidine or spermine.

In some embodiments, the reacting is performed in a solution containing bisulfite ion in a concentration of from about 0.5M to about 2.5M. In further embodiments, the reacting is performed in a solution containing bisulfite ion in a concentration of from about 1M to about 2M.

In some embodiments, the bisulfite salt is magnesium bisulfite. In further embodiments, the reaction further comprises sodium bisulfite. In some embodiments, the reacting is performed at about 40 degrees to about 60 degrees for about 4 to about 15 hours. In some embodiments, the nucleic acid is gDNA.

In some embodiments, the methods of the invention further comprise reacting the bisulfite-treated nucleic acid with a base. In some embodiments, the base is sodium hydroxide (NaOH).

Also provided in accordance with the present invention are kits for use in specific conversion reaction of cytosine to uracil comprising at least one bisulfite salt having the formula $X^+HSO_3^-$ or $Y^{+2}(HSO_3^-)_2$; wherein $X^+$ is ammonium ion, a tetraalkyl; ammonium ion, or a group 1A ion other than sodium; and $Y^{+2}$ is a group 2A ion or a group 7B ion. In some embodiments, $X^+$ comprises at least one of lithium ion, potassium ion, ammonium ion, tetraalkylammonium ion, magnesium ion, manganese ion and calcium ion.

In some embodiments, the kit further comprises a polyamine catalyst. In some embodiments, the polyamine catalyst has the Formula I or II:

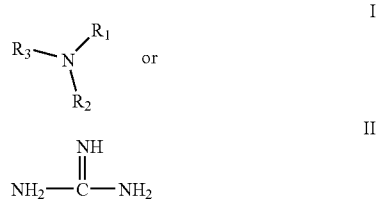

or a salt or derivative thereof, wherein $R_1$, $R_2$ and $R_3$ re each independently —[—$(CH_2)_n$—NH—]$_q$—X; n is 1 to 4; q is 0-3; and X is H or $C_{1-4}$ alkyl; provided that at least one q is not 0.

In some embodiments, the polyamine catalyst comprises at least one of triamines and tetraamines. In further embodiments, the catalyst comprises at least one of diethylene triamine, guanidine and their salts and derivatives. In some embodiments, $R_1$ and $R_2$ are each —$(CH_2)_2$—$NH_2$; and $R_3$ is H.

In some embodiments of the kits of the invention, the bisulfite salt is magnesium bisulfite. In further embodiments, the kits of the invention further comprise sodium bisulfite. In some embodiments, the kits contain premeasured materials useful in various embodiments of the methods of the invention.

In some embodiments, the methylation status of one or more cytosines in the target nucleic acid(s) can be determined by any suitable method. Typically, methylation status can be determined by measuring the presence or relative amount of uracil at a nucleotide position that was previously non-methylated cytosine, and was converted to uracil by the bisulfite treatment. If desired, the presence or relative amount of residual cytosine at the same nucleotide position (indicating the presence of methylcytosine) can be measured for comparison with the amount of uracil, to determine the degree of methylation at the particular nucleotide position. Appropriate control experiments can also be performed to correct for incomplete transformation of cytosine to uracil, if desired.

The presence or amount of uracil and/or methylcytosine at a particular nucleotide position can be measured by any suitable method, such as DNA sequencing (e.g., by the Sanger method or Maxam-Gilbert method or subsequent embodiments thereof (e.g., using dye-labeled terminators or dye-labeled primers, such as discussed in WO 02/30944 and by Ansorge et al. DNA Sequencing Strategies—Automated and Advanced Approaches, John Wiley & Sons, New York, 1997)), PCR (e.g., primer-specific PCR), oligonucleotide ligation assay (OLA) or other ligation-dependent techniques (e.g., see U.S. Pat. No. 6,511,810 and references cited therein), single base extension (over the potential methylation site, mass spectrometry, real time PCR (e.g., using labeled probes that are complementary to C and or U), microarrays comprising sequence specific probes, etc. Various exemplary techniques are also described by Kirk et al., Nucl. Acids Res., 30:3295-3311 (2002).

DETAILED DESCRIPTION

It is to be understood that both the foregoing general description and the following detailed description are exemplary and explanatory only and are not restrictive of the invention, as claimed. In this application, the use of the singular includes the plural unless specifically stated otherwise. In this application, the use of "or" means "and/or" unless stated otherwise. Furthermore, the use of the term "including", as well as other forms, such as "includes" and "included", is not intended to be limiting.

DEFINITIONS

As used herein, the term "gDNA" refers to genomic DNA.

Bisulfite ion has its accustomed meaning of $HSO_3^-$. Typically, bisulfite is used as an aqueous solution of a bisulfite salt, for example magnesium bisulfite, which has the formula $Mg(HSO_3)_2$, and sodium bisulfite, which has the formula $NaHSO_3$.

The term "PCR" is intended to denote polymerase chain reaction, as is well known in the art. The term "MSP" denotes methylation specific PCR, such as described by J. Herman, Proc. Natl. Acad. Sci. 93, 9821-26 (1996), and modified as discussed herein.

As used herein, the term "nucleic acid" includes, for example, nucleobase-containing polymeric compounds, including naturally occurring and non-naturally occurring forms thereof, for example and without limitation, genomic DNA, cDNA, hnRNA, mRNA, rRNA, tRNA, fragmented nucleic acids, nucleic acids obtained from subcellular organelles such as mitochondria or chloroplasts, and nucleic acids obtained from microorganisms, or DNA or RNA viruses that may be present on or in a biological sample.

As used herein, the term "polyamine" is intended to refer to compounds having more than one amine group, and their salts. Thus, "polyamines" include, without limitation, diamines, triamines such as diethylene triamine (DETA), guanidine and tetramethyl guanidine; tetraamines, such as spermine; compounds having the Formula I as disclosed herein, and other compounds containing two or more amine groups, and salts of the same. In some embodiments, the polyamine has a molecular weight of 1000 or less, or a molecular weight of 500 or less, or a molecular weight of 100 or less.

The term "quaternary amine compound" is intended to include, without limitation, salts of quaternary ammonium compounds, including without limitation quaternary alkyl ammonium salts. These include, without limitation, quaternary alkyl ammonium halides, for example quaternary methyl ammonium bromide, quaternary ammonium chlorides, tetraethyl ammonium hydroxide, tetraethylammonium chloride, tetrabutyl ammonium chloride, tetrabutyl ammonium bromide, and the like.

The term "ssDNA" refers to single stranded DNA, resulting typically, but not exclusively, from denaturing double stranded DNA ("dsDNA").

The term "TE buffer" refers to the well-known buffering solution of 10mM tris-cl and 1mM EDTA that is typically used in analysis of nucleic acids.

The term "triamine" refers to compounds having three amino groups, including but not limited to diethylene triamine (DETA), guanidine HCl, tetramethyl guanidine, and the like.

The term "nucleic acid sample" is intended to denote a sample (e.g., a composition, mixture, suspension or solution) that contains at least one nucleic acid.

Unless otherwise specified, reference herein to cytosine refers to unmethylated cytosine and conversion refers to specific conversion of unmethylated cytosine to uracil.

In some embodiments, the present invention provides methods of converting cytosine to uracil in a nucleic acid sample by using a catalyzed bisulfite reaction. The methods of the present invention provide significant benefits.

Typical protocols in the art require the use of freshly made 3M sodium bisulfite, long reaction times of up to 16 hours, and the presence of an antioxidant. Because of the relatively high salt concentration, the low pH of the reaction and the long reaction times, the DNA can be degraded. Additionally, the ss DNA resulting from the gDNA is difficult to purify away from the high concentration of salt used in the reaction. In addition, it is typically necessary to remove most of the bisulfite, which interferes with subsequent enzymatic reactions, for example, those of PCR protocols. Prior procedures also require freshly prepared solutions of bisulfite and antioxidant (typically hydroquinone).

Embodiments of the present invention may overcome one or more disadvantages of prior methods as briefly described below. For example, it has been discovered in accordance with the some embodiments of the present invention that the reaction of a nucleic acid of interest with bisulfite ion, such as magnesium bisulfite, in the presence of a polyamine catalyst affords faster reaction times. In addition, because the reaction time is faster, less oxidation may occur. Thus, the presently disclosed methods do not require addition of an antioxidant such as hydroquinone. Additionally, magnesium bisulfite solutions (e.g., 1M) may remain acidic in the presence of effective concentrations of polyamine catalyst (for example 0.1M DETA), whereas the corresponding solution of sodium bisulfite salt does not. Thus, methods of the invention can employ bisulfite concentrations that are significantly less than used previously, thereby affording facilitated sample preparation for PCR. Moreover, it has been discovered herein that stock magnesium bisulfite solutions can be employed, thus eliminating the need to freshly prepare those solutions. Finally, methods of the invention may reduce or eliminate the need for a separate predenaturation step, and can be performed in a greatly reduced reaction volume. Thus, methods of the present invention can afford PCR yields similar to those of protocols previously known in the art, but with reduced preparation times, reaction times, and clean-up efforts.

Suitable counter-ions for the bisulfite compound may be monovalent or divalent. Examples of monovalent cations include, without limitation, sodium, lithium, potassium, ammonium, and tetraalkylammonium. Suitable divalent cations include, without limitation, magnesium, manganese, and calcium. A more detailed discussion of uses of quaternary amine catalysts is provided in the contemporaneously filed application entitled METHOD AND MATERIALS FOR QUATERNARY AMINE CATALYZED BISULFITE CONVERSION OF CYTOSINE TO URACIL, assigned to the assignee of this application, which is hereby incorporated by reference.

Typically, the product of the reaction between the nucleic acid and bisulfite is reacted with a base to complete the conversion of cytosine to uracil. One typical base is NaOH. In some embodiments the methods herein further comprise the step of purifying the bisulfite-reacted nucleic acid prior to treatment with base. In some further embodiments, the methods further comprise the step of analyzing the product of the bisulfite conversion reaction, for example by mass spectrometry, to confirm completion of the bisulfite conversion reaction.

In certain embodiments, the invention comprises kits for carrying out the methods of the invention. In one embodiment, a kit of the invention includes pre-measured ingredients required for carrying out the bisulfite reaction, such as magnesium bisulfite and catalyst. In certain embodiments, the catalyst comprises DETA. In certain embodiments, the invention includes a kit containing pre-packaged materials sufficient to prepare multiple samples. In yet another embodiment, the materials will be pre-packaged with appropriate Eppendorf tubes or other reaction vessels, as appropriate.

The section headings used herein are for organizational purposes only and are not to be construed as limiting the subject matter described. All documents, or portions of documents, cited in this application, including but not limited to patents, patent applications, articles, books, and treatises, are hereby expressly incorporated by reference in their entirety for any purpose.

The examples described herein are certain embodiments chosen to illustrate the invention. Applicant does not limit the invention to these embodiments. Rather, Applicant acknowledges that those reasonably skilled in the art will readily recognize additional variants that do not differ from the scope and spirit of the invention.

EXAMPLES

The Examples below demonstrate the catalytic utility of the illustrative polyamine, diethylene triamine (DETA). DETA was prepared as a 2M solution in accordance with Japanese patent publication JP 1995265082A, which is hereby incorporated by reference. Other polyamines such as the triamine guanidine, derivatives thereof, and the tetraamine, spermine, were also evaluated, with similar results. Although the use of spermine led to a precipitate, the cytosine to uracil reaction apparently proceeded. The treated nucleic acid product may be further purified if desired, e.g., using an adsorptive technique or dialysis to remove residual reactants.

Ten samples and one control were prepared with the desired bisulfite reagents and DETA as a catalyst and evaluated on two different plates. Odd numbered samples used the template Univ. Me. methylated DNA, while even numbered samples use the #50 Af. Am. unmethylated DNA template. Sample 11 was a Non Template Control (NTC).

The samples were treated in accordance with the protocol of J. Herman, PNAS 93, 9821-26 (1996), except as indicated below. This protocol requires the use of a fresh solution of sodium bisulfite, not more than 30 minutes old, as well as the use of an antioxidant, hydroquinone.

The magnesium bisulfite used in the Examples described herein was purchased as a 2M $Mg(HSO_3)_2$ solution from Aldrich Chemical Co., Milwaukee, Wis. The pH of the purchased solution was 2.6. The solution was used off the shelf, as purchased, and not as a fresh preparation made prior to each use. No antioxidant was used with the magnesium bisulfite. All pH values were measured by pH paper unless otherwise indicated. Sodium bisulfite solutions were made by dissolving solid $NaHSO_3$ in water.

Initial attempts to provide easier desalting during the purification portion of the sodium bisulfite reaction protocol by reducing the amount of bisulfite in the reaction led to incomplete conversion. Evaluation of the catalytic effect of the addition of a triamine to the sodium bisulfite reaction, (the catalyst and the purification are not necessarily connected), showed that the triamine, diethylene triamine, was an effective catalyst. However, it also was surprisingly discovered that an off-the-shelf solution of magnesium bisulfite converted cytosine to uracil similar to reaction with the freshly prepared sodium bisulfite solutions.

TABLE 1

| | Examples 1 & 2 | Examples 3 & 4 | Examples 5 & 6 | Examples 7 & 8 | Examples 9 & 10 |
|---|---|---|---|---|---|
| gDNA (diluted to 50 μL with DI water) | 1 μg | 1 μg | 1 μg | 1 μg | 1 μg |
| 2M NaOH (pre-denaturation step) | 5.5 μL | 5.5 μL | 5.5 μL | 5.5 μL | NA |
| 10 mM Hydroquinone | 30 μL | 30 μL | 30 μL | 30 μL | NA |
| Fresh 3.6M NaHSO$_3$ | 520 μL (to yield 3M) | 520 μL (to yield 3M) | 104.5 μL (to yield 2M) | 31.6 μL (to yield 1M) | NA |
| 2M Mg(HSO$_3$)$_2$ | NA | NA | NA | NA | 85.5 μL To yield approx. 1M (1.3M) |
| 2M DETA | NA | 5.5 μL | 5.5 μL | 5.5 μL | 5.5 μL |
| pH | | | 5.5~6 | 7 | 4 |

The reaction mixtures in Examples 1-2 were made in strict accordance with the Herman protocol noted above. The reaction mixtures in Examples 3-8 were made according to the Herman protocol with the addition of DETA and with the shown reduction in volume of sodium bisulfite solution. Examples 9 and 10 were prepared using magnesium bisulfite, as an off-the-shelf commercially available 2M stock solution, rather than a fleshly prepared sodium bisulfite solution. In contrast to the Herman protocol, the reaction mixtures in Examples 9 and 10 were not previously denatured, the bisulfite solution was not freshly prepared, no antioxidant was used, the pH was not strictly controlled, and initially, reaction times were just four hours. In later experiments, reactions were allowed to proceed for up to 15 hours. The reaction mixture had a pH of 4. The resultant bisulfite-treated DNA was purified in accordance with the Herman protocol (i.e. using the commercially available DNA Wizard clean-up kit and an EtOH/precipitation step overnight).

Once the reactions were complete, two separate analyses were conducted to evaluate whether the reaction products were suitable for PCR. First, a "dilute and PCR" approach was used with a small amount of each sample to obtain qualitative results. Second, a more complete PCR approach benefiting from a purification step was conducted.

Each sample was analyzed by methylation-specific PCR (MSP). MSP provides a relatively fast analysis method for methylation status of bisulfite-treated DNA samples, providing a yes/no answer. The method is based on using primer pair sets. One primer pair is designed to anneal/PCR amplify only if all cytosines were successfully converted to uracil, and the other primer pair in the set annealed/PCR amplified if the methylated cytosine (CpG cytosines only) were methylated, and therefore not converted to uracil.

The MSP pairs that amplify specific gene fragments, and the expected size of the amplicon, are the following:

for the p16 gene, unmethylated reaction (size 151):

5'-TTATTAGAGGGTGGGGTGGATTGT-3' (sense),
(SEQ ID NO:1)

5'-CAACCCCAAACCACAACCATAA-3' (antisense);
(SEQ ID NO:2)

methylated reaction (size 150):

5'-TTATTAGAGGGTGGGGCGGATCGC-3' (sense),
(SEQ ID NO:3)

5'-GACCCCGAACCG-CGACCGTAA-3' (antisense);
(SEQ ID NO:4)

for the MGMT gene, unmethylated reaction (93):

5'-TTTGTGTTTTGATGTTTGTAGGTTTTTGT-3' (sense),
(SEQ ID NO:5)

5'-AACTCCACACTCTTCCAAAAACAAAACA-3' (antisense);
(SEQ ID NO:6)

methylated reaction(81):

5'-TTTCGACGTTCGTAGGTTTTCGC-3' (sense),
(SEQ ID NO:7)

5'-GCACTCTTCCGAAA-ACGAAACG-3' (antisense);
(SEQ ID NO:8)

for the DAP-kinase gene, unmethylated reaction:

5'-GGAGGATAGTTGGATTGAGTTAATGTT-3' (sense),
(SEQ ID NO:9)

5'-CAATCCCT-CCCAAACACCAA-3' (antisense);
(SEQ ID NO:10)

methylated reaction:

5'-GGATAGTCGGATCGAGTTAACGTC-3' (sense),
(SEQ ID NO:11)

5'-CCCTCCCAAACGCCG-3' (antisense);
(SEQ ID NO:12)

for the MLH1 gene, unmethylated reaction (124)

```
5'-TTTTGATGTAGATGTTTTATTAGGGTTGT (sense)
(SEQ ID NO:13)

5'-ACCACCTCATCATAACTACCCACA (antisense)
(SEQ ID NO:14)
``` methylated reaction (115)

```
5'-ACGTAGACGTTTTATTAGGGTCGC (sense)
(SEQ ID NO:15)

5'-CCTCATCGTAACTACCCGCG (antisense)
(SEQ ID NO:16)
``` for the p15 gene, unmethylated reaction (154):

```
5'-TGTGATGTGTTTGTATTTTGTGGTT (sense)
(SEQ ID NO:17)

5'-CCATACAATAACCAAACAACCAA (antisense)
(SEQ ID NO:18)
``` methylated reaction (148)

```
5'-GCGTTCGTATTTTGCGGTT (sense)
(SEQ ID NO:19)

5'-CGTACAATAACCGAACGACCGA (antisense)
(SEQ ID NO:20)
```

The PCR recipe used to evaluate the samples was:

| | |
|---|---|
| 2X Taq Gold PCR Master Mix | 10 µL |
| Fwd primer (5 uM) | 1 µL |
| Rev primer (5 uM) | 1 µL |
| Bisulfite treated DNA | 0.5 µL |
| H2O | 7.5 µL |
| | 20 µL |

2X TaqGold PCR master mix is commercially available from Applied Biosystems. The forward and reverse primer sequences are those listed above.

The following thermal cycling schedule was used:

| | |
|---|---|
| 40 cycles | 95 deg 5 min |
| | 95 deg 30 sec |
| | 60 deg 45 sec |
| | 72 deg 1:00 min |
| | 4 deg forever |

One of the primers in each set was synthesized with a 5' FAM label. A 1 µL aliquot of the above PCR reaction was added to HiDi formamide with ROX 500 size standard added, and denatured by heating at 95° C. for 5 min. By using a FAM-labeled primer, the PCR amplicon was directly analyzed on an ABI PRISM® 310 Genetic Analyzer, with POP-4™ polymer, using run module "GS POP4 (1mL) A" (reagents and instrument all from Applied Biosystems).

The presence of a PCR amplicon (i.e. a "peak") having the correct size as observed using the 310 Genetic Analyzer indicated a successful reaction. Additionally, the height or area of the peak could be used empirically to determine how much template (i.e. bisulfite-treated gDNA) was initially present. The bigger the peak, the more DNA was initially present.

If bisulfite-conversion is incomplete, MSP can sometimes give a "false positive" or an overestimate in the amount of cytosine methylation due to the counting of unreacted cytosine nucleobases as methyl-cytosine nucleobases (see e.g. Table 2, p16U, sample 3, below). Accordingly, control reactions can be performed to establish conditions that afford substantially quantitative conversion of cytosine to uracil nucleobases. Alternatively, control reactions can be performed to measure the efficiency of the conversion, to allow subtraction of unreacted, non-methylated cytosine nucleobases from experimental results so that the amount of methylation can be determined more accurately. For example, synthetic DNA containing non-methylated cytosine can be used to assess the conversion yield to uracil following bisulfite treatment. For example, an 80% yield obtained with synthetic DNA would indicate that correction factor of 20% should be applied (subtracted) from the amount of methylated cytosine that is observed experimentally for a sample of interest.

The results in Table 2 show that the efficiency of the conversion reaction of cytosine to uracil nucleobases was improved by the addition of the polyamine catalyst, DETA. PCR yields in all cases were similar to or greater than those obtained with the uncatalyzed 3M sodium bisulfite treated sample lacking polyamine catalyst. Furthermore, the results indicate that 2M sodium bisulfite with catalyst produces yields similar to, or better than, the catalyzed 3M sodium bisulfite yields. Poorer results were obtained using 1M sodium bisulfite, even with catalyst.

The Applicant(s) have discovered that good conversion yields can be obtained using $Mg(HSO_3)_2$ (e.g., 1M concentration), optionally with a polyamine catalyst, and without addition of hydroquinone or other antioxidant. For example, PCR yields with $Mg(HSO_3)_2$ have been found to be at least comparable or superior to yields obtained using sodium bisulfite yields at concentrations of 2M to 3M.

This finding is surprising and unexpected, particularly in view of the fact that the magnesium bisulfite solution need not be made fresh, as is usually required for the sodium bisulfite solution. Initially, it was possible that the off-the-shelf magnesium bisulfite solution would suffer from degradation to $SO_2$, which would account for the low pH seen initially. Accordingly, it was predicted that the magnesium bisulfite treated samples would not achieve effective PCR yields. However, the data in Table 2 demonstrates results quite to the contrary.

TABLE 2

| | 1 | 2 | 3 | 4 | 5 | 6 | 7 | 8 | 9 | 10 | NTC Ctrl 11 |
|---|---|---|---|---|---|---|---|---|---|---|---|
| p16 M | X | X | 1200 | X | 1600 | X | X | X | X* | X | X |
| p16 U | Small peak | 4500 | 5600 | X | 5600 | X | X | X | X | 4000 | 4000 |

TABLE 2-continued

|  | 1 | 2 | 3 | 4 | 5 | 6 | 7 | 8 | 9 | 10 | NTC Ctrl 11 |
|---|---|---|---|---|---|---|---|---|---|---|---|
| mgmt M | 6000 | X | 6000 | X | 6000 | X | X | X | 6000 | X | X |
| mgmt U | X | 1600 | X | 2000 | X | 2000 | X | X | X | 5000 | X |
| mlh 1 M | 2000 | X | 2000 | X | 2000 | X | X | X | 2000 | X | X |
| mlh 1 U | X | 1600 | X | 1600 | X | 1600 | X | X | X | 2000 | X |
| er M | 2400 | X | 2400 | X | 2400 | X | X | X | 2400 | X | X |
| er U | X | Very small | X | 1600 | X | 1600 | X | X | X | 1400 | X |
| p14 M | ~400 | X | 2000 | X | 2000 | *2000** | 6000 | *6000* | 6000 | X | X |
| p14 U | X | 3000 | X | 3000 | X | 7000 | X | X | X | 6000 | X |
| gstp M | 300 | X | 500 | X | 300 | X | X | X | 200 | X | X |
| gstp U | X | 5000 | X | 5000 | X | 5000 | X | X | X | 2000 | X |
| dapk M | 2000 | X | 2000 | X | 2000 | *2000* | X | X | 2000 | X | X |
| dapk U | X | 3000 | X | 5000 | X | 7000 | X | X | X | 3200 | X |
| p15 M | 2000 | X | 2000 | X | 2000 | X | X | X | 3200 | X | X |
| p15 U | X | 400 | X | 200 | X | 800 | X | X | X | 1600 | X |

*Bold italics indicates unexpected result

The MSP-PCR product was then sometimes sequenced for further "resolution". DNA sequencing was performed using standard protocols and reagents from Applied Biosystems.

Prior to sequencing of the PCR amplicon, the primers and excess dNTPs used during the MSP-PCR were removed by treatment of a 4 μL aliquot of the PCR reaction with an equal volume mixture containing 2 Units each of Shrimp Alkaline Phosphatase (SAP) and exonuclease 1 (exo) (USB Corporation, Cleveland, Ohio). The reaction was incubated at 37° C. for 1 hr, and then heat-denatured at 75° C. for 15 mm. A 4 μL aliquot of the exo/SAP reaction was added to a solution containing 1-4 μL of BigDye® Terminator v1.1 cycle sequencing reaction mix (Applied Biosystems), 2 μL of BigDye® Terminator v1.1 5X sequencing buffer, 2 μL of the reverse PCR primer (5 uM) (which did not have a FAM-label), and enough water for a final volume of 12 μL. Thermal cycling: 95° C./1 min, 50 cycles of 96° C./10 sec, 52° C./10 sec, 60° C./4 mm, and stored at 4° C. The cycle-sequencing reaction products were purified by an Edge Biosystems Performa® 96-well plate, dried under vacuum, dissolved in 20 μL of HiDi Formamide and analyzed on an ABI PRISM® 3730 DNA Analyzer with KB basecaller or a 3700 DNA Analyzer.

DNA sequencing permitted evaluation of each cytosine in the gene region that was amplified by the MSP primer sets, allowing assessment of the degree of cytosine to uracil conversion.

The studies herein utilized 2M magnesium bisulfite stock solutions, which were diluted with the sample to produce a final magnesium bisulfite concentration of about 1M. Use of a more concentrated magnesium bisulfite solution would yield higher bisulfite concentration for conversion, while still keeping reaction volumes to a minimum. Such increased bisulfite concentration in the reaction mixture could easily be employed, and would be expected to enhance bisulfite conversion of cytosine to uracil. The optimization of such reaction parameters, including volume and/or concentration of magnesium bisulfite solution, temperature, pH and other reaction conditions are expected to lead to more complete conversion, and are well within the skill of the art.

To verify that the magnesium bisulfite reaction is specific for cytosine but not methyl cytosine, a model system was created. A synthetic, four base oligonucleotide, ATCG, was employed to determine the rate of conversion by HPLC. On a ds Eclipse HP column, using 0.1M TEAA=A and 0.1M TEAA with 25% CH$_3$CN=B. ATCG and AT$^{Me}$CG were treated in accordance with the catalyzed magnesium bisulfite reaction described above and directly analyzed by HPLC to evaluate the specificity of the reaction. The results indicated that after 22 minutes, at 50° C., the catalyzed 1M magnesium bisulfite treated ATCG reacted to yield ATUG. Under the same reactions conditions, the AT$^{Me}$CG did not react. Thus, these results indicate that the catalyzed magnesium bisulfite reaction is specific for the conversion of unmethylated cytosine to uracil. Accordingly, utilization of magnesium bisulfite can have great utility in methylation assessment.

Further tests performed with 0.06-0.1M DETA provided similar results. The pH reached 5-7 when 0.2, 0.26, and 0.33M DETA was used. In the 0.26 and 0.33M samples, a precipitate was formed, but it was not detrimental to the reactions.

In addition to DETA, the guanidine based triamines guanidine HCl (0.27M-0.6M) and tetramethylguanidine (0.2M) also were used. The guanidine compounds are denaturants to help maintain single stranded DNA during bisulfite conversion. The model HPLC system is not useful in studying the effect of denaturation.

In some further experiments, the denaturant TBAC or TBAB, alone, and in combination with DETA were employed. For example, bisulfite conversion of gDNA was carried out successfully using a mixture of TBAC and DETA.

It also was observed using HPLC that NaOH added to the magnesium bisulfite reaction increased the rate of reaction of the oligonucleotide ATCG, due to the raised pH. The results presented herein also show that magnesium bisulfite, even without catalyst, converts cytosine to uracil. The preferred pH range of this conversion reaction is about 2.6-4.0. Raising pH beyond this range typically results in an undesirable precipitate.

Also useful is a new clean-up procedure, employing size exclusion, which appears to improve product yields, as described in a separate patent application by the present inventors entitled, "Improved Bisulfite Method" (U.S. application Ser. No. 60/498,996 filed Aug. 29, 2003, and also application Ser. No. 60/520,941 filed Nov. 11, 2003 having the same title and filed concurrently herewith) each of which is hereby incorporated by reference in its entirety. Although the antioxidant, hydroquinone, is not required in the magnesium bisulfite reactions, and in light of these findings may not be needed in the sodium bisulfite reactions, it can be used without negative effect in the methods of the invention.

The inventors are not limited to these embodiments or any of the examples above described herein, but rather acknowledge that other variants of these methods will be apparent to those skilled in the art and are within the scope and spirit of the invention disclosed herein.

Other variants of the catalyzed bisulfite reactions described herein will be apparent to those of reasonable skill in the art and area considered within the scope and spirit of the invention and disclosed and claimed herein.

What is claimed is:

1. In a method of converting at least one cytosine nucleobase to a uracil nucleobase in a nucleic acid wherein the nucleic acid is treated with bisulfite ion, the improvement comprising:
performing said treatment of the nucleic acid with bisulfite ion in the presence of $Mg^{2+}$ ion.

2. The method of claim 1, wherein said treatment is performed in a solution containing magnesium bisulfite in a concentration of from about 0.5M to about 2.5M.

3. The method of claim 2, wherein said solution contains magnesium bisulfite in a concentration of 1M to 2M.

4. The method of claim 1, wherein said treatment is performed at 40 degrees to 60 degrees for 4 to 15 hours.

5. The method of claim 1, wherein said nucleic acid is gDNA.

6. The method of claim 1, wherein said nucleic acid is obtained from microorganisms.

7. The method of claim 2, wherein said nucleic acid is obtained from DNA or RNA viruses.

8. The method of claim 1, further comprising treating the product of said reaction of said nucleic acid and said bisulfite ion with a base.

9. The method of claim 8, wherein said base comprises NaOH.

10. A kit for use in converting at least one cytosine nucleobase to a uracil nucleobase in a nucleic acid wherein the nucleic acid is treated with bisulfite ion, the improvement comprising:
performing said treatment of the nucleic acid with bisulfite ion in the presence of $Mg^{2+}$ ion.

11. The kit of claim 10, wherein the bisulfite ion and the $Mg^{2+}$ ion are present as magnesium bisulfite.

12. The kit of claim 10, wherein said treatment is performed in a solution containing magnesium bisulfite in a concentration of from about 0.5M to about 2.5M.

13. The kit of claim 10, wherein said solution contains magnesium bisulfite in a concentration of 1M to 2M.

14. The kit of claim 10, wherein said treatment is performed at 40 degrees to 60 degrees for 4 to 15 hours.

15. The kit of claim 10, wherein said nucleic acid is gDNA.

16. The kit of claim 10, wherein said nucleic acid is obtained from microorganisms.

17. The kit of claim 10, wherein said nucleic acid is obtained from DNA or RNA viruses.

18. The kit of claim 10, further comprising treating the product of said reaction of said nucleic acid and said bisulfite ion with a base.

19. The kit of claim 18, wherein said base comprises NaOH.

* * * * *

SEQUENCE LISTING

<160> NUMBER OF SEQ ID NOS: 20

<210> SEQ ID NO 1
<211> LENGTH: 24
<212> TYPE: DNA
<213> ORGANISM: Artificial Sequence
<220> FEATURE:
<223> OTHER INFORMATION: sense

<400> SEQUENCE: 1
ttattagagg gtggggtgga ttgt                                           24

<210> SEQ ID NO 2
<211> LENGTH: 22
<212> TYPE: DNA
<213> ORGANISM: Artificial Sequence
<220> FEATURE:
<223> OTHER INFORMATION: antisense

<400> SEQUENCE: 2
caaccccaaa ccacaaccat aa                                             22

<210> SEQ ID NO 3
<211> LENGTH: 24
<212> TYPE: DNA
<213> ORGANISM: Artificial Sequence
<220> FEATURE:
<223> OTHER INFORMATION: sense

<400> SEQUENCE: 3
ttattagagg gtggggcgga tcgc                                           24

<210> SEQ ID NO 4
<211> LENGTH: 21
<212> TYPE: DNA
<213> ORGANISM: Artificial Sequence
<220> FEATURE:
<223> OTHER INFORMATION: antisense

<400> SEQUENCE: 4
gaccccgaac cgcgaccgta a                                              21

<210> SEQ ID NO 5
<211> LENGTH: 29
<212> TYPE: DNA
<213> ORGANISM: Artificial Sequence
<220> FEATURE:
<223> OTHER INFORMATION: sense

<400> SEQUENCE: 5
tttgtgtttt gatgtttgta ggttttttgt                                     29

<210> SEQ ID NO 6
<211> LENGTH: 28
<212> TYPE: DNA
<213> ORGANISM: Artificial Sequence

```
<220> FEATURE:
<223> OTHER INFORMATION: antisense

<400> SEQUENCE: 6
aactccacac tcttccaaaa acaaaaca                                              28

<210> SEQ ID NO 7
<211> LENGTH: 23
<212> TYPE: DNA
<213> ORGANISM: Artificial Sequence
<220> FEATURE:
<223> OTHER INFORMATION: sense

<400> SEQUENCE: 7
tttcgacgtt cgtaggtttt cgc                                                  23

<210> SEQ ID NO 8
<211> LENGTH: 22
<212> TYPE: DNA
<213> ORGANISM: Artificial Sequence
<220> FEATURE:
<223> OTHER INFORMATION: antisense

<400> SEQUENCE: 8
gcactcttcc gaaaacgaaa cg                                                   22

<210> SEQ ID NO 9
<211> LENGTH: 27
<212> TYPE: DNA
<213> ORGANISM: Artificial Sequence
<220> FEATURE:
<223> OTHER INFORMATION: sense

<400> SEQUENCE: 9
ggaggatagt tggattgagt taatgtt                                              27

<210> SEQ ID NO 10
<211> LENGTH: 20
<212> TYPE: DNA
<213> ORGANISM: Artificial Sequence
<220> FEATURE:
<223> OTHER INFORMATION: antisense

<400> SEQUENCE: 10
caatccctcc caaacaccaa                                                      20

<210> SEQ ID NO 11
<211> LENGTH: 24
<212> TYPE: DNA
<213> ORGANISM: Artificial Sequence
<220> FEATURE:
<223> OTHER INFORMATION: sense

<400> SEQUENCE: 11
ggatagtcgg atcgagttaa cgtc                                                 24

<210> SEQ ID NO 12
<211> LENGTH: 15
<212> TYPE: DNA
<213> ORGANISM: Artificial Sequence
<220> FEATURE:
<223> OTHER INFORMATION: antisense

<400> SEQUENCE: 12
ccctcccaaa cgccg                                                           15
```

```
<210> SEQ ID NO 13
<211> LENGTH: 29
<212> TYPE: DNA
<213> ORGANISM: Artificial Sequence
<220> FEATURE:
<223> OTHER INFORMATION: sense

<400> SEQUENCE: 13
ttttgatgta gatgttttat tagggttgt                                              29

<210> SEQ ID NO 14
<211> LENGTH: 24
<212> TYPE: DNA
<213> ORGANISM: Artificial Sequence
<220> FEATURE:
<223> OTHER INFORMATION: antisense

<400> SEQUENCE: 14
accacctcat cataactacc caca                                                   24

<210> SEQ ID NO 15
<211> LENGTH: 24
<212> TYPE: DNA
<213> ORGANISM: Artificial Sequence
<220> FEATURE:
<223> OTHER INFORMATION: sense

<400> SEQUENCE: 15
acgtagacgt tttattaggg tcgc                                                   24

<210> SEQ ID NO 16
<211> LENGTH: 20
<212> TYPE: DNA
<213> ORGANISM: Artificial Sequence
<220> FEATURE:
<223> OTHER INFORMATION: antisense

<400> SEQUENCE: 16
cctcatcgta actacccgcg                                                        20

<210> SEQ ID NO 17
<211> LENGTH: 25
<212> TYPE: DNA
<213> ORGANISM: Artificial Sequence
<220> FEATURE:
<223> OTHER INFORMATION: sense

<400> SEQUENCE: 17
tgtgatgtgt ttgtattttg tggtt                                                  25

<210> SEQ ID NO 18
<211> LENGTH: 23
<212> TYPE: DNA
<213> ORGANISM: Artificial Sequence
<220> FEATURE:
<223> OTHER INFORMATION: antisense

<400> SEQUENCE: 18
ccatacaata accaaacaac caa                                                    23

<210> SEQ ID NO 19
<211> LENGTH: 19
<212> TYPE: DNA
<213> ORGANISM: Artificial Sequence
<220> FEATURE:
<223> OTHER INFORMATION: sense
```

```
<400> SEQUENCE: 19
gcgttcgtat tttgcggtt                                                    19

<210> SEQ ID NO 20
<211> LENGTH: 22
<212> TYPE: DNA
<213> ORGANISM: Artificial Sequence
<220> FEATURE:
<223> OTHER INFORMATION: antisense

<400> SEQUENCE: 20
cgtacaataa ccgaacgacc ga                                                22
```